United States Patent [19]

Kabara

[11] Patent Number: 5,208,257
[45] Date of Patent: May 4, 1993

[54] TOPICAL ANTIMICROBIAL PHARMACEUTICAL COMPOSITIONS AND METHODS

[76] Inventor: Jon J. Kabara, 414 Green St., Galena, Ill. 61036

[21] Appl. No.: 902,767

[22] Filed: Jun. 23, 1992

Related U.S. Application Data

[63] Continuation of Ser. No. 509,316, Apr. 13, 1990, abandoned, which is a continuation of Ser. No. 266,202, Oct. 27, 1988, abandoned, which is a continuation-in-part of Ser. No. 136,540, Dec. 22, 1987, abandoned, which is a continuation of Ser. No. 854,154, Apr. 21, 1986, abandoned.

[51] Int. Cl.$^5$ .................. A61K 31/23; A61K 31/20
[52] U.S. Cl. ........................ 514/552; 514/558
[58] Field of Search ........................ 514/552, 558

[56] References Cited

U.S. PATENT DOCUMENTS

| | | | |
|---|---|---|---|
| 1,772,975 | 8/1930 | Wieland | 167/53 |
| 2,154,449 | 4/1939 | Hoffman et al. | 99/90 |
| 2,190,714 | 2/1940 | Hoffman et al. | 99/224 |
| 2,466,663 | 4/1949 | Russ et al. | 167/53 |
| 2,729,586 | 1/1956 | Peck | 167/68 |
| 2,752,284 | 6/1956 | Berliner et al. | 167/58 |
| 3,404,987 | 10/1968 | Kooistra et al. | 99/150 |
| 3,959,491 | 5/1976 | Young et al. | 424/317 |
| 4,002,775 | 1/1977 | Kabara | 424/532 |
| 4,067,997 | 1/1978 | Kabara | 424/532 |
| 4,156,719 | 5/1979 | Sezaki et al. | 424/118 |
| 4,160,820 | 7/1979 | Wagenknecht et al. | 424/48 |
| 4,187,286 | 2/1980 | Marcus | 424/44 |
| 4,242,359 | 12/1980 | Cooper et al. | 424/325 |
| 4,247,552 | 1/1981 | Hallesy et al. | 424/250 |
| 4,277,461 | 7/1981 | Lucker et al. | 424/44 |
| 4,277,475 | 7/1981 | Vickery | 424/250 |
| 4,298,624 | 11/1981 | Mehring et al. | 424/532 |
| 4,299,826 | 11/1981 | Luedders | 424/181 |
| 4,322,399 | 3/1982 | Ahmad et al. | 424/44 |
| 4,335,115 | 6/1982 | Thompson et al. | 424/181 |
| 4,343,788 | 8/1982 | Mustacich et al. | 424/78 |
| 4,343,798 | 8/1982 | Fawzi | 424/240 |
| 4,360,013 | 11/1982 | Barrows | 128/130 |
| 4,368,186 | 1/1983 | Vickery et al. | 424/78 |
| 4,371,518 | 2/1983 | Gazzani | 424/78 |
| 4,392,848 | 7/1983 | Lucas et al. | 128/213 |
| 4,406,884 | 9/1983 | Fawzi et al. | 424/81 |
| 4,410,442 | 10/1983 | Lucas et al. | 252/107 |
| 4,430,381 | 2/1984 | Harvey et al. | 427/412 |
| 4,439,441 | 3/1984 | Hallesy et al. | 424/273 |
| 4,474,678 | 10/1984 | Lutz et al. | 252/174.21 |
| 4,476,141 | 10/1984 | Cormier | 424/321 |
| 4,479,795 | 10/1984 | Mustacich et al. | 604/53 |
| 4,489,097 | 12/1984 | Stone | 424/318 |
| 4,551,148 | 11/1985 | Riley, Jr. et al. | 604/890 |
| 4,722,941 | 2/1988 | Eckert et al. | 424/532 |
| 5,093,140 | 3/1992 | Watanabe | 424/326 |

FOREIGN PATENT DOCUMENTS 0143245 9/1984 European Pat. Off. .

(List continued on next page.)

OTHER PUBLICATIONS

Kabara, Cosmetic & Drug Preservation, pp. 275-304, 1984.

(List continued on next page.)

*Primary Examiner*—Leonard Schenkman
*Attorney, Agent, or Firm*—Harness, Dickey & Pierce

[57] ABSTRACT

The present invention discloses a topical antimicrobial and anti-parasite pharmaceutical composition and methods of using the same. The topical antimicrobial pharmaceutical composition includes a safe and effective amount of an ethoxylated or propoxylated glycerol fatty acid ester and a pharmaceutically acceptable carrier. Also disclosed is a topical antimicrobial pharmaceutical composition including a safe and effective amount of a tertiary mixture including, a glycerol fatty acid ester, a binary mixture of fatty acids including a first fatty acid antimicrobial agent selected from $C_6$ to $C_{18}$ fatty acids, and a second fatty acid antimicrobial agent selected from $C_6$ to $C_{18}$ fatty acids, and a pharmaceutically acceptable carrier. Further disclosed is a topical antimicrobial pharmaceutical composition including a safe and effective amount of an ethoxylated or propoxylated glycerol fatty acid ester, a binary fatty acid mixture including, a first fatty acid antimicrobial agent selected from $C_6$ to $C_{18}$ fatty acid and the second fatty acid antimicrobial agent selected from $C_6$ to $C_{18}$ fatty acids, where the second fatty acid is not the same as the first fatty acid, and a pharmaceutically acceptable carrier. Further disclosed is a method of treating and preventing microbial related skin conditions in humans or lower animals comprising topically applying, to the afflicted situs of a human of lower animal in need of such treatment, a safe and effective amount of the above composition.

18 Claims, No Drawings

FOREIGN PATENT DOCUMENTS

| | | |
|---|---|---|
| 0161425 | 3/1985 | European Pat. Off. . |
| 2755052 | 12/1977 | Fed. Rep. of Germany . |
| 634749 | 12/1978 | Switzerland . |
| 641829 | 8/1979 | Switzerland . |
| 1481961 | 3/1974 | United Kingdom . |

OTHER PUBLICATIONS

Satjoowsici et al., Polyoxyethylene Esters of Fatty Acids, Ch. 5, pp. 142–174 (1966).

Shick, Norionic Surfactants, Marcel Dekker, Inc., New York, 1966, Chap. 28, pp. 958–960.

Diversey Wyandotte Corp., "Before & After Pre-milking and Post-milking Teat Dip" (1976).

Diversey Wyandotte Corp., "Before & After TM Sanitizing Pre-milking and Post-milking Teat Dip" (1974).

Richard L. Boddie and Stephen C. Nickerson, "Efficacy of a Fatty Acid–Lactic Acid Postmilking Teat Germicide in Reducing Incidence of Bovine Mastitis" (1980).

CA92(7):57080e, JP 54034061 (1979).

CA99(3):21158s, JP 58063357 (1983).

CA89(9):74466r, JP 53010141 (1978).

CA99(19):157083w, JP 58111669 (1983).

C. Nieman, "Influence of Trace Amounts of Fatty Acids on the Growth of Microorganisms," *Bacteriol. Rev.*, 18:147–163 (1954).

F. W. Chattaway and C. C. Thompson, "The Action of Inhibitors on Dermatophytes," *Biochem. J.*, 63:648–656 (1956).

Kabara, J., *A New Preservative System For Food*, Journal of Food Safety, vol. 4, pp. 13–25, 1982.

Branan, A., & Davison, P., *Antimicrobials in Foods*, Marcel Dekker, New York, 1983, pp. 109–140.

Kabara, J., *Fatty Acids and Derivatives as Antimicrobial Agents—A Review*, AOCS Monograph No. 5, pp. 1–14, 1978.

Schick, M. J., *Nonionic Surfactants*, Marcel Dekker, Inc., New York, 1966, Chap. 28, Sec. 13, pp. 958–960.

Dillan K., *Effects of the Ethylene Oxide Distribution on Nonionic Surfactant Properties*, JAOCS, vol. 62, No. 7, pp. 1144–1985, 1982.

"Efficacy of a Fatty Acid–Lactic Acid Postmilking Teat Germicide in Reducing Incidence of Bovine Mastitis," Richard L. Boddie and Stephen C. Nickerson pp. 799–801 Oct., 1988.

Kabara, Jr., *Medium–Chain Fatty Acids and Esters as Antimicrobial Agents*, Cosmetic and Drug Preservation, pp. 275–304, 1984.

Kabara, J., *Toxicological, Bactericidal and Fungicidal Properties of Fatty Acids and Some Derivatives*, The Journal of the American Oil Chemists's Society, vol. 56, No. 11, pp. 760A–767A, 1979.

Kabara, J., *Inhibition of Staphylococlus Aureus in a Model Agar–Meat System by Monolaurin: A Research Note*, Journal of Food Safety, vol. 6, pp. 197–201, 1984.

Kabara, J., *Antimicrobial Agents Derived from Fatty Acids*, JAOCS, vol. 61, No. 2, pp. 397–403, 1984.

Kabara, J., *GRAS Antimicrobia Agents for Cosmetic Products*, Journal of the Society of Cosmetic Chemists, vol. 31, pp. 1–10, 1980.

Schemmel, R., Lynch, P., Krohn, K., & Kabara, J., *Monolaurin as an Anticaries Agent*, 1985.

Kabara, Jr., Ohkawa, M., Ikekawa, T., Katori, T., & Mishikawa, Y., *Examination of Antitumor, Immunological and Plant–Growth Inhibitory Effects of Mongycerides of Caprylic, Capric, and Lauric Acids and Related Compounds*, Pharacological Effects of Lipids, vol. II, pp. 263–272, 1985.

Li, C., & Kabara, J., *Effects of Lauricidin on Fomes Annosus and Phellinus Weirii*, AOCS Monograph No. 5, pp. 45–47, 1978.

Kenney, D., *Cosmetic Formulas Preserved With Food–Grade Chemicals*, Cosmetics and Toiletries, Part I, vol. 97, pp. 71–76, 1982.

Kabara, J., & Wernette, C., *Cosmetic Formulas Preserved with Food–Grade Chemicals*, Cosmetics and Toiletries, Part II, vol. 97, pp. 77–84, 1982.

"Pure and Applied Chemistry," *The Official Journal of the International Union of Pure and Applied Chemistry*, Butterworths, London, 1:245, 247, 249 (1960).

Prince, H. N., "Effect of pH on the Antifungal Activity of Undecylenic Acid and its Calcium Salt," New Jersey (1959).

TOPICAL ANTIMICROBIAL PHARMACEUTICAL COMPOSITIONS AND METHODS

RELATED APPLICATIONS

This is a continuation of U.S. patent application Ser. No. 509,316, filed Apr. 13, 1990, which is a continuation of Ser. No. 266,202, filed Oct. 27, 1988, which is a continuation-in-part of 136,540, filed Dec. 22, 1987, which is a continuation of 854,154, filed Apr. 21, 1986, all abandoned.

TECHNICAL FIELD

The present invention relates generally to topical pharmaceutical compositions and, more particularly, to primarily aqueous solutions exhibiting unique antimicrobial and/or anti-parasitic properties.

BACKGROUND OF THE INVENTION

The use of antimicrobial agents plays an important part in current medical therapy. This is particularly true in dermatology, where the most effective course of treatment for skin, mucous membranes, hair lesions, or infections frequently includes the use of a topical antimicrobial agent. The present invention includes topical compositions and methods which provide unique performance against a broad spectrum of microbes with excellent speed.

Various carboxylic acids are known to be good antimicrobial agents. However, when these acidic solutions are directly applied to an animal's skin, they may interfere with wound healing, cause irritation, inflammation or the like. Also, these solutions have poor solubility properties in water which, in turn, limits the efficacy of aqueous solutions employing these materials.

It is also well recognized that there is presently a need for a mild antimicrobial or anti-parasitic which can be safely applied to skin and mucous membranes, such as an animal's teats, ears, and eyes, that will be substantially harmless to the applied area but which will eliminate, arrest, or substantially reduce the growth of bacteria, fungi, mold and the like. The instant invention meets this need.

The art discloses that several different carboxylic acid are generally useful in the suppression of fungi, bacteria, molds, and the like growth. U.S. Pat. No. 4,406,884 issued to Fawzi discloses a topical antimicrobial composition in the form of an aqueous gel or lotion. This composition contains $C_5$-$C_{12}$ fatty acids and has a pH no greater than about 5. U.S. Pat. No. 4,343,798 issued to Fawzi, teaches a topical antimicrobial anti-inflammatory composition having a pH less than about 5 and containing $C_5$-$C_{12}$ fatty acids together with a corticosteroid component. U.S. Pat. No. 4,489,097 issued to Stone, teaches the addition of anti-fungal/antibacterial materials to sterile compositions. The antifungal/antibacterial material disclosed is a $C_4$-$C_9$ carboxylate antimicrobial agent having a pH of about 6.0 or below. U.S. Pat. No. 4,410,442 issued to Lucas, et al. teaches solutions for use with hydrophilic soft contact lenses containing $C_5$-$C_{12}$ fatty acids, especially octanoic acid. U.S. Pat. No. 4,392,848 issued to Lucas, et al. teaches a catheter having a liquid reservoir of an antimicrobial agent flowing through the lumen of the catheter. The antimicrobial agent disclosed is a straight-chain carboxylic acid or carboxylic acid salt having a $C_4$-$C_9$ chain. U.S. Pat. No. 4,430,381 issued to Harvey, et al. teaches a process for imparting antimicrobial properties to a material. The antimicrobial being a $C_3$-$C_{12}$ alkane, alkene or alkyne monocarboxylate. U.S. Pat. Nos. 4,343,788 and 4,479,795, both issued to Mustacich, et al. teach medical polymers that provide diffusion for certain carboxylate antimicrobial agents. U.S. Pat. No. 4,002,775 issued to Kabara teaches a food grade microbicidal composition having a monoester with a $C_{12}$ aliphatic fatty acid as its primary microbicide. U.S. Pat. No. 1,772,975 issued to Weiland teaches the use of lactic acid, acetic acid, or combinations thereof, as antiseptics at properly adjusted pH levels. U.S. Pat. No. 2,154,449 issued to Hoffman et al. teaches the use of aliphatic $C_3$-$C_{12}$ carboxylic acids and their salts as mold inhibitors in food compositions. U.S. Pat. No. 2,190,714 issued to Hoffman, et al. teaches the addition of a $C_3$-$C_{12}$ carboxylic acid to inhibit growth food products other than margarine and sourdough bread. U.S. Pat. No. 3,404,987 to Kooistra, et al. teaches an antimicrobial containing edible mineral salt and edible acid preservative substances, particularly propionic acid. U.S. Pat. No. 2,466,663 issued to Russ, et al. teaches the use of a topical or intravenous caprylic acid solution to combat mycotic infections or growths. U.S. Pat. No. 2,729,586 issued to Peck teaches a therapeutic composition having at least one salt of a $C_3$-$C_{11}$ monocarboxylic acid and water soluble chlorophyll.

Other materials also disclose the use of fatty acids for the suppression of fungi, bacteria, mold and the like. Kabara, J., *Medium-chain Fatty Acids and Esters as Antimicrobial Agents*, Cosmetic and Drug Preservation, Pgs. 275–304, 1984, teaches the use of $C_6$-$C_{22}$ saturated and unsaturated fatty acids as antimicrobials. Kabara, J., *Toxicological, Bactericidal and Fungicidal Properties of Fatty Acids and Some Derivatives*, The Journal of the American Oil Chemists' Society, Vol. 56, No. 11, Pages 706A–767A (1979) teaches the applying of fatty acids to animal skin and eyes. Some fatty acids were found to be skin and eye irritants. Kabara, J., *Inhibition of Staphylococlus Aureus In a Model Agar-Meat System By Monolaurin: A Research Note*, Journal of Food Safety, Vol. 6, Pgs. 197–201 (1984), teaches the use of monolaurin as a food preservative to combat microorganisms. Kabara, J., *Antimicrobial Agents Derives from Fatty Acids*, JAOCS, Vol. 61, No. 2, Pgs. 397–403 (1984) teaches the use of saturated and unsaturated fatty acids as antimicrobial agents. Kabara, J., *GRAS Antimicrobia Agents for Cosmetic Products*, Journal of the Society of Cosmetic Chemists, Vol. 31, Pgs. 1–10 (1980), teaches the composition of monolaurin, a phenol, di-tert-butyl anisole, and a chelating agent such as ethylenediaminetetracetic acid to be useful in destroying gram positive and gram negative bacteria. Schemmel, R., Lynch, P., Krohn, K., and Kabara, J., *Monolaurin as an Anticaries Agent*, teaches the use of glycerolmonolaurin in inhibiting development of smooth surface caries in rats innoculated with Streptococcus mutants. Kabara, Jr., Ohkawa, M., Ikekawa, T., Katori, T., and Mishikawa, Y., *Examination on Antitumor, Immunological and Plant-Growth Inhibitory Effects of Monoglycerides of Caprylic, Capric, and Lauric Acids and Related Compounds*, Pharacological Effects of Lipids, Volume II, Pgs. 263–272 (1985) teaches the use of the monoglycerides or caprylic, capric and lauric acids for regulating antitumor, immunological, and plant-growth activity. Li, C., and Kabara, J., *Effects of Lauricidin on Fomes Annosus and Phellinus Weirii*, AOCS Monograph No. 5, Pgs. 45–47 (1978) teaches the use of monolaurin in combating root rot fungi in coniferous forest. Kenney, D., *Cosmetic Formulas Preserved With Food-Grade Chemicals*, Cosmetics and Toiletries, Part 1, Vol. 97, Pgs. 71-76 (1982) and Kabara, J. and Wernette, C., *Cosmetic Formulas Preserved with Food-Grade Chemicals*, Cosmetics and Toiletries, Part II, Vol. 97, Pgs. 77-84 (1982) teaches the use of monoglyceride emulsifier, food-grade phenols and a chelator in the preservation of cosmetics. Kabara, J., *A New Preservative System For Food*, Journal of Food Safety, Volume 4, Pgs. 13-25 (1982) teaches the use of monolaurin, a food grade phenolic, and a chelator as an antimicrobial for the preservation of food. Branan, A. and Davison, P. *Antimicrobials in Foods*, Marcel Dekker, New York 1983, Pgs. 109-140 teaches the use of saturated, unsaturated and esters of fatty acids as antimicrobials and the use of these compounds for food preservation. Kabara, J., *Fatty Acids and Derivatives as Antimicrobial Agents—Review*, AOCS Monograph No. 5, Pgs. 1-14 (1978) teaches the use of saturated, unsaturated and esters of fatty acids as antimicrobials and the use of these compounds for permeating microorganism cellular membranes for killing the microorganism.

The art also teaches many methods of ethoxalation. *Nonionic Surfactants*, Schick, M. J., Marcel Dekken, Inc., New York (1966) and Dillan, K., *Effects of the Ethylene Oxide Distribution on Nonionic Surfactant Properties*, JAOCS, Vol. 62, No. 7, Pgs. 1144-1151 (1985) teach the ethoxalation of primary alcohols to produce nonionic surfactants. All of the above references herein are incorporated by reference.

The above discussion clearly reflects the ambiguous state of the art with regard to the suitability and selection of fatty acid-based materials as antimicrobials, especially in the topical or preservative mode. The art disclosed materials vary widely in their efficacy and possess an even wider variety of side effects, particularly when employed in veterinary topical materials under adverse or stressful conditions. Many of these materials are also viewed as corrosive. (The term glyceryl and glycerol are used interchangeably herein when describing fatty acid esters.)

SUMMARY AND DETAILED DESCRIPTION OF THE INVENTION

The present invention relates to preservative pharmaceutical compositions and methods, especially those useful when applied topically and/or those which exhibit good shelf stability. The present invention relates to the discovery that unique overall antimicrobial properties and pharmaceutical acceptability of certain glycerol fatty acid esters can be achieved or improved by either (1) the addition of certain ether groups, particularly ethoxy and propoxy units; (2) by use in combination with select fatty acid mixtures; or (3) a combination of (1) and (2). Glycerol fatty acid ester materials modified as described retain or exhibit an improved or increase in overall spectrum and speed of activity while producing fewer or reduced (in severity) side effects. Such a material is especially useful when compared to the unmodified material in that it produces much less irritation at the site of application.

The present invention further relates to the discovery that the spectrum and speed of activity of both modified and unmodified fatty acid esters can be significantly improved when used in a tertiary mixture or in combination with a mixture of two or more select $C_6$-$C_{18}$ fatty acids, preferably $C_6$-$C_{12}$ saturated fatty acids and $C_{13}$-$C_{18}$ unsaturated fatty acids. All these materials are in turn employed in combination with a topical carrier. Such materials provide effective topical antimicrobial activity and are accordingly useful in the treatment and prevention of conditions which are caused, or aggravated by microbial organisms (including viruses) or parasites on skin and mucous membranes or are otherwise related to microbes or parasites.

Also, the compositions of the present invention exhibit exceptional preservative applications. In addition to preserving the final composition and stabilizing the material to increase the efficacy in cold climate or conditions, the present compositions provide outstanding preservative characteristics when added primarily as a preservative in food stuffs, cosmetic formulations and pharmaceutical compositions (topical; parenteral; intramuscular; and intravenous). The preservative applications are further discussed in my copending United States patent application entitled "ANTIMICROBIAL PRESERVATIVE COMPOSITIONS AND METHODS", U.S. Ser. No. 754,155, filed Apr. 21, 1986, the same date as one of the parents of the present application, and which is expressly and wholly incorporated herein by reference.

For example, such compositions are useful in veterinary applications as a teat dip, an eye medication, or an ear medication by applying a safe and effective amount of the compositions, described above, to an animal in need of such antimicrobial, antiviral or anti-parasitic treatment on the area to be treated one or more times daily. The compositions are also useful as spermatostatic or spermatocidal agents in humans and other mammals and are accordingly useful in contraceptive methods.

It is well known that in general the ethoxylation or propoxylation of an antimicrobial agent generally renders that agent biologically inactive; at a minimum, the activity is substantially reduced. See *Nonionic Surfactants*, Martin J. Schick, Marcel Dekker, Inc., New York, N.Y. Chap. 28, Pgs. 958-960.

Unexpectedly, it has been found that the addition of a select or small number of ethoxy or propoxy units to a glyceryl fatty acid ester results in an antimicrobial agent which retains its activity and demonstrates reduced side effects such as less irritation. Further, it has been discovered that the formed narrow range ethoxylates possess better surface-active properties when compared with the broad distribution range adducts and therefore lend themselves to better formulations. Also, the narrow range ethoxylates seem to have a better detergent activity than the broad distribution adducts. Also, this retained germicidal and detergent activity does not correlate with what is expected of non-ionic ethoxylates. Generally, non-ionic ethoxylates such as TWEEW 80 and SPAN 20 are germicidally inactive. While not intending to be bound by theory, it appears that controlled ethoxylation or propoxylation adds to available hydroxyl radicals by ring cleavage with regeneration of the hydroxyl group. This reaction is an addition reaction without termination. Such ethoxylation is discussed in more detail in Dillan, K., *Effects of the Ethylene Oxide Distribution of Nonionic Surfactant Properties*, JAOCS, Vol. 62, Pgs. 1144-1151, 1985, which is herein incorporated by reference.

The fatty acid ester or glyceryl fatty acid ester which is to be ethoxylated or propoxylated for use in the compositions and methods of the present invention is preferably selected from the group consisting of polyhydric alcohols, polyglycerols, sucrose, glucose, sorbitol, propylenediol and fatty acid esters or glyceryl fatty acid esters having about six to about twenty-one carbon atoms including the fatty acid moety; however, it is possible for the non-fatty acid moiety of useful materials to have 3 to 30 carbon atoms itself. Preferably, the material is a glyceryl fatty acid ester wherein the alcohol or non-fatty acid moiety has 3 carbon atoms, and the fatty acid moiety is saturated having from about 6 to about 12 carbon atoms. The highly preferred compounds include monocaprylin, monocaprin and monolaurin and mixtures thereof. Monolaurin is most highly preferred taking into account cost, availability and activity.

The fatty acid esters or glyceryl fatty acid esters are ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective. Most preferably, the ethoxylation compound is selected from the group consisting of ethylene oxide, propylene oxide and mixtures thereof.

The fatty acid esters or glyceryl fatty acid esters are ethoxylated or propoxylated under controlled conditions preferably within a narrow range according to conventional methods, such as those in the Dillan article, further incorporated by reference. The glyceryl fatty acid esters are ethoxylated or propoxylated by a suitable amount of ethoxylate or propoxylate compound. While lower levels may be useful, in a preferred embodiment, the ethoxylation or propoxylation compound is reacted at a level of about 0.25 to about 5, more preferably about 0.25 to about 4, still more preferably at about 0.5 to about 3.0 moles, yet still more preferably about 0.25 to about 2 moles, and, still more preferably, at about 0.25 to about 1.0 moles of ethoxylate or propoxylate per mole of glyceryl ester. Thus, the resulting products useful in the compositions and methods of the present invention generally contain at least about 1 mole of ethoxylate or propoxylate per four moles of glyceryl ester; in other words there is at least about one-quarter, and preferably at least about one-half, either unit or moeity per glyceryl fatty acid ester unit or molecule. This could be further expressed as stating that useful ethoxylated glyceryl fatty acid esters of the present invention are esters wherein at least one-quarter, and preferably at least one-half of the total glyceryl ester has reunited with at least one ethoxy or propoxy moeity.

Generally, the adduct formed by the reaction of the glyceryl fatty acid ester and ethoxylation or propoxylation compound occurs as described in the art. However, it is noted that the reaction products are complex and may be formed by other well known conventional processes in the chemical art. For example, the of glycerol portion and fatty acid portion may be ethoxylated or propoxylated separately prior to making the final ester.

The ethoxylation or propoxylation adds at least one-quarter, one-half or more ethoxy or propoxy units to the glyceryl fatty acid ester. Preferably the ethoxylation adds about 0.25 to 6, more preferably 0.25 to 3, more preferably 0.25 to 2 and, still more preferably, 0.25 to 1 ethoxy or propoxy units per final unit of glyceryl fatty acid ester. This generally corresponds to about 0.25 to about 6 moles of ethoxy or proxy compound per mole of glyceryl fatty acid ester.

The pharmaceutical compositions of the present invention employ a safe and effective amount of ethoxy/propoxy modified glyceryl ester adduct in combination with a suitable pharmaceutically-acceptable topical carrier. Such compositions preferably employ about 0.001 to about 20%, more preferably, about 0.1 to about 10% and, still more preferably, about 1 to about 5%, of the ester by weight of the carrier or final composition. However, levels as low as, for example, about 0.001 to about 0.01 are effective amounts and may be employed for a single component agent, e.g as monolaurin, especially when employed in certain compositions, such as when an alcohol such as ethenol, propanol or isopropanol is present.

As discussed above, it has been further observed that a combination of a glyceryl fatty acid ester compound (either ethoxylated/propoxylated and non-ethoxylated/propoxylated) in a mixture with at least one and preferably two or more acids selected from the group consisting of $C_6$–$C_{18}$ fatty acids also demonstrates unique activity. Also, other polyols such as polyglyceryl, sucrose, glucose, sorbitol, and the like sugar esters have been found to work satisfactorily when substituted for the glyceryl fatty acid ester. The useful fatty acid esters or glyceryl fatty acid esters include those selected from the groups consisting of fatty acid esters or glyceryl fatty acid esters having three to thirty carbon atoms in the non-fatty acid moiety portion of the molecule; those that are monesters and contain 3 carbon atoms are preferred. The preferred glyceryl fatty acid ester compounds therefore include materials such as monocaprylin, monocaprin, monolaurin and mixtures thereof. These materials may also be modified by the addition of one or more ethoxy/propoxy units as described herein prior to being employed in the combination. The tertiary mixtures useful herein comprise a glyceryl fatty acid ester, (which may optionally be ethoxylated/propoxylated as described herein); a first fatty acid compound; and a second fatty acid compound. The preferred first and second fatty acid compounds for use in such tertiary mixtures or combinations are preferably straight chain materials and include, without limitation, $C_6$–$C_{12}$ saturated and $C_{13}$–$C_{18}$ unsaturated fatty acids. The highly preferred saturated fatty acids include, caproic, heptanoic, caprylic, pelargonic, capric, undecanoic, lauric myristic, palmitic, heptadacanoic and stearic thereof. The most preferred materials include carproic, heptanoic, caprylic, capric, undecanoic, and lauric. Highly preferred materials include heptanoic, caprylic and capric.

The preferred $C_{13}$–$C_{18}$ unsaturated fatty acid are those having one or two cis-type double bonds possessing the cis configuration, and mixtures of these materials. Highly preferred materials include myrystoleic, palmitoleic, linoleic, linolenic, and mixtures thereof.

It is preferred that the addition of the fatty acid components to the glyceryl fatty acid ester compound (including the ethoxylated/propoxylated compounds) improve the activity of the final composition or system as compared to the monester alone. It is also preferred that the fatty acid components additionally aid in the solubility of the glyceryl fatty acid ester compound in aqueous systems and reduce its tendency to cause skin irritation.

The glyceryl fatty acid esters, first fatty acid, and second fatty acid are added to a pharmaceutically-acceptable topical carrier in safe and effective amounts. In a preferred embodiment, they are present at a wt:wt ratio of ester: total fatty acid compounds of about 1:10 to about 10:1; more preferably about 1:10 to about 1:1, and still more preferably about 1:10 to about 1:5 with the glyceryl ester being present at a level of about 0.5 to about 5.0%; more preferably about 0.1 to about 2.0%; and still more preferably about 0.5 to about 1.0% of the final composition.

The glyceryl fatty acid esters may be ethoxylated or propoxylated under controlled conditions according to conventional methods, such as described above for use in the combination or mixture.

The compositions of the present invention can be prepared and applied in any suitable form, but are preferably prepared in forms including, without limitation aqueous solutions, lotions, balms, gels, salves, ointments, boluses, suppositories, and the like. Accordingly, the composition and methods may additionally employ conventional compatible pharmaceutically-acceptable carrier materials useful for such applications. It is desirable that the carrier selected be capable of codissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like. A preferred carrier is generally comprised of alcohols, chelating agents, surfactants, parabens, phenolics and water.

The alcohols useful in the compositions and methods of the present invention may be selected from the group consisting of propylene glycol, phenoxyethanol, methanol, ethanol, isopropyl alcohol, and mixtures thereof. In a preferred embodiment they are selected from the group consisting of propylene glycol, isopropyl alcohol, and mixtures thereof.

Surfactants useful in the compositions and methods of the present invention include those selected from the group consisting of sarcosinates, dioctyl sodium sulfosuccinate, pluronic F68, sodium lauryl sulfate, sorbitan monolaurate, lauryldimethylamineoxide, lauric-diethanolamide, PEG-Esters (polyethylene glycol-dilaurate), coconut hydroxyethyl imidazoline, sodium sulfosuccinate ester of lauric MEA, sodium sulfosuccinate ester of ethoxylated lauryl alcohol, lauric-monoethanolamide, bis-(2-hydroxyethyl) cocoamine oxide. IPA, bis-(2-hydroxyethyl) tallowamine oxide. IPA, dimethylcocoamine oxide. IPA, dimethylcocoamine oxide, (negative inhibitors), polyoxypropylene bases, coconut fatty acid, 2-sulfo-ester, sodium salt, N-coconut oil acyl-N-methyl taurine, sodium salt, lauroyl sarcosine, 30% sodium lauryl sarcosinate, sodium lauroyl sarcosinate, myristoyl sarcosine, oleoyl sarcosine, stearoyl sarcosine, polyoxyethelene 21 stearyl ether (0.1 BHA & 0.005% citric acid as preservatives), lauroamphoglycinate, lauroamphocarboxyglycinate, lauroamphocarboxypropinate, lauroamphocarboxyglycinate-sulfanate, sodium lauryl sulfate (66% lauryl, 27% myristyl, 71% cetyl), polyoxyethylene sorbitan mono-oleate, and mixtures thereof. In a preferred embodiment they are dioctyl sodium sulfosuccinate, sarcosinates, amine oxides, pluronics, pluronic F68, sodium lauryl sulfate, and mixtures thereof, more preferred are pluronic F68, sodium lauryl sulfate, amine oxides, and mixtures thereof.

Chelating agents useful in the compositions and methods of the present invention include those selected from the group consisting of EDTA, EDTA (Na)$_2$, EDTA (Na)$_4$, TEA, lactic acid, lactic acid, polyphosphoric acid and mixtures thereof. In a preferred embodiment, they are lactic acid, polyphosphoric acid and its salts, citric acid, EDTA(Na)$_2$, EDTA (Na)$_4$, TEA, and mixtures thereof, more preferred are lactic acid, EDTA(Na)$_2$, EDTA(Na)$_4$, citric acid and mixtures thereof, highly preferred are lactic acid and its salts, polyphosphoric acid and its salts, EDTA(Na)$_2$, EDTA(Na)$_4$, and mixtures thereof.

Phenols or parabens useful in the compositions and methods of the present invention may be selected from the group consisting of methyl and propyl parabens. These may possess the methyl alone or in combination with 1 propyl paraben; or 4 methyl and 1 propyl; and mixtures thereof (and ester). Also, useful food-grade phenols are BHA or BHT.

Water q.s. may form the remainder of the carrier and is selected from the group consisting of sterile water, distilled water, deionized water, tap and well water. In a preferred embodiment, they are sterile water, distilled water or deionized water. Emulsions may also be employed.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

The alcohols discussed above may be employed in the compositions and methods of the present invention at any suitable level. In a preferred embodiment, they are present at a level of about 5 to about 60%, more preferred at about 10 to about 30 and, in a highly preferred embodiment, at about 20 to about 25% and, in a highly preferred embodiment, at about 5 to about 10% by weight per volume of use solution or about 5 to about 20% by weight per volume of a concentrate.

The surfactants discussed above may be employed in the compositions and methods of the present invention at any suitable level. In a preferred embodiment, they are present at a level of about 0.25 to about 20%, more preferred at about 2 to about 10% and, highly preferred, at about 1% to about 8%, weight per volume of use solution and about 4% to about 20% in a concentrate.

The phenols or parabens discussed above may be employed in the compositions and methods of the present invention at any suitable level. In a preferred embodiment, they are present at a level of about 0.05 to 0.5%, more preferred, at about 0.1 to about 0.5% and, highly preferred, at about 0.1 to about 0.3%, weight per volume of solution.

The chelators discussed above may be employed in the compositions of the present invention at any suitable level. In a preferred embodiment, they are present at a level of about 0.05 to about 7.5%, and more preferably at about 0.1 to about 6%%.

The compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anaesthetics, or anti-inflammatory agents), or may contain materials useful in physically formulating various dosage forms of the present invention, such as excipients, dyes, perfumes, thickening agents, stabilizers, skin penetration enhancers, preservatives, or antioxidants.

In the practice of the method of contraception in the female mammal utilizing the aforementioned compositions, it is expedient to administer an effective spermacidal amount of the compositions of the present invention in a suitable formulation intravaginally, preferably prior to coitus. The preferred dosage range of the compositions of the present invention is from about 0.5 to about 5.0 grams/100 ml of active composition for each vaginal administration for a typical adult human subject. For smaller mammals, or in sustained release applications, the amount would be increased or reduced correspondingly.

For administration according to the aforementioned method one would employ a pharmaceutical composition that is otherwise standard in the art for intravaginal spermatostatic or spermatocidal type contraception. This would typically include the active composition and a dissipating agent or means. These would include, for example, vaginal suppositories, vaginal tablets, vaginal creams, vaginal spray-foams, vaginal soluble waffles, vaginal sponges, effervescing materials, vaginal tampons and the like, as well as slow or sustained release formulations such as implants. Each of these compositions would contain an effective amount of the active spermacidal ingredients in a pharmaceutically acceptable non-toxic carrier or excipient normally employed for such formulations. Typical excipients for solid formulations include, for example, starch, glucose, lactose, mannitol, magnesium stearate, talc, cellulose, magnesium carbonate, sodium bicarbonate, citric acid, and the like. For semi-solid formulations such as suppositories, excipients such as polyalkylene glycols, modified vegetable oils or soft gelatin capsules containing, e.g. vegetable oil, mineral oil or polyalkylene glycol formulations may be employed. For liquid or liquid-type formulations such as creams, jellies, foams, and the like, there may be used water, saline solution, aqueous dextrose, glycerol, higher alcohols, mineral oil, lanolin, gums of vegetable origin, polyalkylene glycols and propellants such as those of the Freon type. The compositions may contain between about 0.0005 to about 10.0 percent by weight of the active ingredient per unit dose, preferably between about 0.5 and 2.0 percent by weight, and may, if desired, contain other active ingredients. Additionally, the above compositions may be utilized in conjunction with other contraceptive methods such as barrier methods, e.g. the condom or diaphragm.

Topical antimicrobial, antiviral and anti-parasite treatment regimens according to the practice of this invention comprise applying a safe and effective amount of the compositions described herein directly to the infected or at-risk skin or mucous membrane; particularly; in a veterinary use, on the teats, eyes, ear areas or at any other situs particularly susceptible to microbial contamination. The solution may be sprayed, dipped, wiped, dropped, poured, toweled, or the like, onto the area to be treated. Application can be made once, or preferably several times daily, to prevent bacteria, fungi, mold, mites or the like from forming or remaining on the animal's skin, teats, ears and eyes.

EXAMPLE 1

The following formulae have been found to be active against a substantial group of organisms. Also, these formulae have been found to be substantially non-irritating as an ear preparation.

| | |
|---|---|
| Ethoxylated Glycerol Monolaurin (Monolaurin EO) or Monolaurin | 0.05–1.0% |
| Caprylic/Capric Acid Mixture | 0.1–5.0% |
| Parabens | 0.0–0.3% |
| Pluronic F68 | 1.0–10% |
| Phenoxylethanol | 0.0–1.0% |
| EDTA (Na)$_2$ | 0.05–0.3% |
| Water | 82.4–98.65% |

Glycerol monolaurin is ethoxylated by about one mole ethylene oxide per mole of glycerol monolaurin by conventional ethoxylation methods as described herein.

EXAMPLE 1a

| | % Weight |
|---|---|
| Monolaurin | 0.25 |
| Caprylic/Capric Acid Mixture | 1.25 |
| Lactic Acid | 1.50 |
| Pluronic F-68 | 2.50 |
| Isopropanol 99% | 15.00 |
| Deionized H$_2$O | 79.50 |

EXAMPLE 2

The following concentrate formula has been found to be active against a selective group of organisms, especially bovine mastitis pathogens. Also, the concentrate formula has been found to be non-irritating when applied as a teat dip.

| | |
|---|---|
| Ethoxylated Glycerol Monolaurin or Monolaurin | 0.5–2.0% |
| Caprylic/Capric Acid Mixture | 0.5–8.0% |
| Phenoxyethanol | 0.0–2.5% |
| Propylene Glycol | 10–30% |
| Parabens | 0.0–1.0% |
| Pluronic F68 | 5–13.0% |
| EDTA (Na)$_2$/Lactic Acid | 1–15% |
| H$_2$O | 30–80% |

Monolaurin is ethoxylated by about 0.5 to about 1.5 mole of ethylene oxide by conventional methods.

EXAMPLE 2a

| | % Weight |
|---|---|
| Monolaurin | 1.00 |
| Caprylic/Capric Acid Mixture | 5.00 |
| Lactic Acid | 6.00 |
| Pluronic F-68 | 10.00 |
| Propylene Glycol | 20.00 |
| FDC Yellow #6 | 0.30 |
| Purified Water USP | 57.00 |

Also, the above formulas (Examples I and II) may be used in human or veterinary protocols, e.g., in the treatment of nasal tissue disease, ophthalmic disease, fungal infections, pulmonary disease, genital infections, and otitis externa. The formulas may be used in insecticidal or germicidal formulation on human or animal skin and plants, catheters, in egg washing, diapers, and wood preservatives. The formulas are also effective as anti-parasitic compositions in combating fowl mites, ear mites, and ticks.

The above formulas are effective against yeasts, gram negative and gram positive organisms and protozoan, more particularly: C. albicans, C. parapsilosis, S. cerevisiae, E. coli, Ps. aeruginosu, S. epidermitis, S. aureus, Bacillus subtilis, Streptococcus faecalis, Streptococcus pyogenec, Corynebacterium, Strep mutans, Trichomonus vaginalis, Streptococcus uberis and Streptococcus agalactiae.

EXAMPLE 3

The following formula concentrate was tested against a yeast, a gram negative and a gram positive organism:

|  | % Weight |
|---|---|
| Monolaurin EO | 1.0 |
| Caprylic and Capric Mixture | 1.5 |
| Propylene Glycol | 22 |
| Parabens | 0.5 |
| Phenoxyethanol | 2.5 |
| Pluronic F-68 | 5.0 |
| EDTA (NA)$_2$ | 2.0 |
| dH$_2$O | q.s. |

After the formula was diluted 1:10 in water, the dilute was introduced to E. coli and to C. parapsilosis organisms. The results are as follows:

| Time | Colony Forming Units/ml |
|---|---|
| *E. COLI* | |
| T$_o$ | 4.3 × 10$^6$ |
| T-2 min. | <30 |
| T-10 min. | <30 |
| *C. PARAPSILOSIS* | |
| T$_o$ | 1.7 × 10$^6$ |
| T-2 min. | 2.5 × 10$^3$ |
| T-10 min. | <30 |

The formula of Example III was diluted 1:20 in water and then the dilute was introduced to S. aureus. The results are as follows:

| *S. AUREUS* | |
|---|---|
| Time | Colony Forming Units/ml |
| T$_o$ | 1.6 × 10$^6$ |
| T2 min. | <5.0 × 10$^1$ |
| T10 min. | <30 |

The above formula of Example III was diluted 1:8 with water and prophylatically applied to a cow's teats twice a day. As a result, upon analyzing the cow's teats, no substantial growth of micro-organisms was found on the teats. The same treatment was conducted on a cow's teats when the ambient air temperature was substantially below 40° F., and substantially similar results were found. It will be appreciated that substantial growth would normally be found.

EXAMPLE 4

|  | % Weight |
|---|---|
| Formula 4-1 | |
| Monolaurin | 1.0 |
| Monolaurin EO | 1.75 |
| Caprylic and Capric Mixture | 5.0 |
| Pluronic F-68 | 13.0 |
| EDTA (NA)$_2$ | 4.0 |
| H$_2$O | 75.25 |
| Formula 4-2 | |
| Monolaurin EO | 1.75 |
| Caprylic and Capric Mixture | 6.0 |
| Pluronic F-68 | 13.0 |
| Lactic Acid (85%) | 15.0 |
| H$_2$O | 64.25 |

After the formulas of Example 4-1 and 4-2 were diluted 1:8 in water the dilute was introduced to *Strep Agalactial* and *Staph Aureus* organisms. The results illustrate the log reduction of organisms after two minutes of exposure with the dilute. Also listed are the log reduction results of other solutions used in the field.

| Log Reduction Of Organisms | | | |
|---|---|---|---|
|  | Time | Strep Agalactial | Staph Aureus |
| Example 4-1 | T = 2 min. | 3.1 | 2.7 |
| Example 4-2 | T = 2 min. | 4.3 | 5.1 |
| Tegragon (Quaternary complex) | T = 2 min. | 1.0 | 2.0 |
| Teat Care (Chlorhexadine) | T = 2 min. | 1.7 | 2.0 |
| All Day (Sorbic Acid) | T = 2 min. | — | 1.8 |
| Quartermate (2000 Lodophor) | T = 2 min. | 2.2 | 2.4 |

The following formula were tested against the identified organisms with the following results.

EXAMPLE 5

The following formula were tested against the identified organisms with the following results.

| Formula 5 | |
|---|---|
|  | % Weight |
| Monolaurin EO | 0.15 |
| Caprylic and Capric Mixture | 0.30 |
| Parabens | 0.05 |
| Dowanol | 0.1 |
| Pluronic F-68 | 5.0 |
| EDTA (Na)$_2$ | 0.1 |
| EDTA (Na)$_4$ | 0.1 |
| dH$_2$O | 94.2 |

| Time | Colony Forming Units/ml |
|---|---|
| *Ps AERUGINOSA* | |
| T$_o$ | 1.2 × 10$^6$ |
| T$_2$ | <30 |
| T$_{10}$ | <30 |
| *E. COLI* | |
| T$_o$ | 3.0 × 10$^6$ |
| T$_2$ | <30 |
| T$_{10}$ | <30 |

EXAMPLE 6

The following formula was tested against the identified organism with the following results.

|  | % Weight |
|---|---|
| Monolaurin EO | 0.15 |
| Caprylic and Capric Mixture | 0.30 |
| Dowanol | 0.10 |
| Pluronic F-68 | 5.0 |
| EDTA (Na)$_2$ | 0.1 |
| EDTA (Na)$_4$ | 0.1 |
| dH$_2$O | 94.25 |

-continued

| Time | Colony Forming Units/ml |
|---|---|
| *Ps AERUGINOSA* | |
| $T_o$ | $1.2 \times 10^6$ |
| $T_2$ | <30 |
| $T_{10}$ | <30 |
| *E. COLI* | |
| $T_o$ | $3.0 \times 10^6$ |
| $T_2$ | <30 |
| $T_{10}$ | <30 |

While the above summarizes the present invention, it will become apparent to those skilled in the art that modifications, variations and alterations may be made without deviating from the scope and spirit of the present invention as described and claimed herein.

What is claimed is:

1. A topical antimicrobial or antiparasitic pharmaceutical composition comprising a safe and effective amount of a mixture comprising:
   (a) a glycerol monoester of lauric acid present in an amount of about 0.05 to about 2.0 percent by weight of the composition;
   (b) a binary mixture of fatty acids comprising:
      (i) a first fatty acid comprising capric acid, and
      (ii) a second fatty acid comprising caprylic acid;
   wherein (a) and (b) are present at a level such that the weight:weight ratio of (a):(b) is about 10:1 to 1:10, and wherein (i) and (ii) are present in a weight:weight ratio of about 1:10 to about 10:1 and said binary mixture is present in an amount of about 0.5 to about 8.0 percent by weight of the composition:
   (c) a pharmaceutically-acceptable carrier which includes lactic acid; and
   (d) a surfactant which comprises a block copolymer of propylene oxide and ethylene oxide.

2. A topical pharmaceutical composition according to claim 1 wherein said monoester is present at a level of about 0.1 to about 1 percent of the composition.

3. A topical pharmaceutical composition according to claim 1 wherein said monoester is present at a level of about 1 percent of the composition.

4. A topical pharmaceutical composition according to claim 1 wherein said carrier additionally comprises at least one additional carrier component selected from the group consisting of alcohols, parabens, phenols, water, and mixtures thereof.

5. A method of treating and preventing microbial-, viral-, or parasite-related skin conditions in humans or lower animals comprising topically applying to the afflicted situs of a human or lower animal in need of such treatment a safe and effective amount of a composition according to claim 4.

6. A topical pharmaceutical composition according to claim 1 wherein the pharmaceutical carrier additionally comprises an alcohol selected from the group consisting of propylene glycol, phenoxyethanol, methanol, ethanol, isopropyl alcohol, and mixture thereof.

7. A topical pharmaceutical composition according to claim 6 wherein said alcohol or alcohols are present in an amount of about 5 percent to about 60 percent by volume.

8. A topical pharmaceutical composition according to claim 1 wherein a second chelating agent is present and is selected from the group consisting of polyphosphoric acid and its salts, EDTA, EDTA(Na)$_2$, EDTA(Na)$_4$, citric acid and its salts, and mixtures thereof.

9. A topical pharmaceutical composition according to claim 1 wherein the surfactant is selected from the group consisting of dioctyl sodium sulfosuccinate, sarcosinates, amine oxides, Pluronics, sodium lauryl sulfate and mixtures thereof.

10. A topical pharmaceutical composition according to claim 1 wherein the pharmaceutical carrier additionally comprises a paraben selected from the group consisting of methyl parabens, propyl parabens, BHA, BHT, and mixtures thereof.

11. A topical pharmaceutical composition according to claim 10 wherein said phenols or parabens are present in an amount of about 0.05 percent to 0.5 percent by weight.

12. A topical pharmaceutical composition according to claim 1 wherein the surfactant is present at a level of about 0.25 percent to about 20 percent by weight.

13. A topical pharmaceutical composition according to claim 1 wherein a chelating agent is present in an amount of about 0.05 percent to about 7.5 percent by weight.

14. The topical pharmaceutical composition according to claim 1 wherein said monoester is monolaurin.

15. The topical pharmaceutical composition according to claim 1 wherein the glyceryl ester has been ethoxylated or propoxylated at a level of at least about 0.25 to about 5 moles of ethoxylate or propoxylate per mole of glyceryl ester.

16. A method of treating and preventing microbial-, viral- or parasite-related skin conditions in humans or lower animals comprising topically applying to the afflicted situs of a human or lower animal in need of such treatment a safe and effective amount of a composition according to claim 1.

17. A method of treating and preventing mastitis in an animal in need of such treatment or prevention comprising applying a composite according to claim 1 to at least one test of said animal.

18. A topical antimicrobial or antiparasitic pharmaceutical composition comprising a safe and effective amount of a mixture comprising:
   (a) a polyhydric alcohol monoester of lauric acid present in an amount of about 0.05 to about 2.0 percent by weight of the composition;
   (b) a binary mixture of fatty acids comprising:
      (i) a first fatty acid comprising capric acid, and
      (ii) a second fatty acid comprising caprylic acid;
   wherein (i) and (ii) are present in weight:weight ratio of about 1:10 to about 10:1 and said binary mixture present in an amount of about 0.5 to about 8.0 percent by weight of the composition;
   (c) a pharmaceutically-acceptable carrier which includes a chelating agent; and
   (d) a surfactant which comprises a block copolymer of propylene oxide and ethylene oxide and which is present at a level of about 0.25 to about 10% by weight.

* * * * *